(12) United States Patent
Ishak

(10) Patent No.: US 11,013,845 B1
(45) Date of Patent: May 25, 2021

(54) SYSTEMS AND METHODS FOR PLASMA SEPARATION AND UV IRRADIATION

(71) Applicant: Noshi Ishak, Gilford, NH (US)

(72) Inventor: Noshi Ishak, Gilford, NH (US)

(*) Notice: Subject to any disclaimer, the term of this patent is extended or adjusted under 35 U.S.C. 154(b) by 0 days.

(21) Appl. No.: 16/931,489

(22) Filed: Jul. 17, 2020

(51) Int. Cl.
*A61M 1/34* (2006.01)
*A61M 1/30* (2006.01)

(52) U.S. Cl.
CPC .......... *A61M 1/3496* (2013.01); *A61M 1/30* (2013.01); *A61M 1/3479* (2014.02); *A61M 2205/053* (2013.01)

(58) Field of Classification Search
CPC .... A61M 1/30; A61M 1/3479; A61M 1/3496; A61M 1/36; A61M 1/3681; A61M 1/3683; A61M 1/3686; A61M 2205/053
See application file for complete search history.

(56) References Cited

U.S. PATENT DOCUMENTS

| | | | |
|---|---|---|---|
| 2001/0024623 A1* | 9/2001 | Grimm | A61L 2/10 422/44 |
| 2004/0127841 A1* | 7/2004 | Briggs | A61M 1/3681 604/6.01 |
| 2010/0331753 A1* | 12/2010 | Gandini | A61M 1/3621 604/5.02 |
| 2013/0178834 A1* | 7/2013 | Greenberg | A61M 1/3687 604/522 |
| 2019/0015578 A1* | 1/2019 | Smyczynski | A61M 1/3681 |
| 2020/0030790 A1* | 1/2020 | Dodd | A61M 1/3683 |

FOREIGN PATENT DOCUMENTS

DE 3624511 A1 * 5/1987 ............... A61L 2/10

OTHER PUBLICATIONS

Machine Translation of DE 36 24 511 (Year: 1987).*
Screenshot from O3UV website o3uv.com, accessed Feb. 4, 2021.

* cited by examiner

*Primary Examiner* — Benjamin J Klein
(74) *Attorney, Agent, or Firm* — Catherine Napjus; Michael Persson; Chisholm, Persson & Ball, PC

(57) ABSTRACT

The present invention is a UV light box, systems, and methods for irradiating plasma.

17 Claims, 11 Drawing Sheets

SYSTEMS AND METHODS FOR PLASMA SEPARATION AND UV IRRADIATION

FIELD OF THE INVENTION

The present invention relates generally to viral and bacterial infection treatment, and specifically to said treatment by the separation and UV irradiation of infected blood plasma.

BACKGROUND

Ultraviolet (UV) radiation is a potent source of energy, known to be capable of neutralizing or killing any virus or bacteria. It is frequently used to sterilize water and disinfect surfaces in hospitals, clinics, dental offices, restaurants, factories, and many other places where disinfection is of primary importance. In the medical field, UV light is used to sterilize medical equipment in operating rooms and patient consultation areas. It is also used for water sterilization for dialysis and in labs. UV light is used on the skin to treat skin ailments.

UV radiation also has a history with blood irradiation for the purpose of killing bacterial and viral infections. This process is commonly referred to as UV Blood Irradiation (UBI). Anecdotal UBI studies have shown that exposing a small amount of blood briefly to UV light successfully treated several different types of infections. A brief history of UBI is provided in the following article: Michael R. Hamblin, *Ultraviolet Irradiation of Blood: "The Cure That Time Forgot"?*, 996 ADV. EXP. MED BIOL. 295 (2018). The discovery of vaccines and the development of antibiotics has slowed or halted further studies into UBI. The treatment may still have use with antibiotic-resistant strains of bacteria; novel viruses or viruses with no developed vaccine; and venoms, however. The application to virus treatment is of particular interest, considering that, as of this writing, the world is within the grip of a novel coronavirus pandemic, which currently has no proven vaccine or treatment.

Blood has several components. Plasma represents about 55% of blood and is mainly water, but also includes proteins, ions, nutrients, and wastes. Importantly, during viral or bacterial infections, it is the plasma that carries the infective organisms. Plasma may be further broken down into two components. The first component, which is referred to herein as "small plasma," contains valuable proteins, such as albumin, small immunoglobulins, and antibodies. The second component, which is referred to herein as "large plasma," contains larger proteins, large immunoglobulins, and lipids, such as LDL and microbes, such as bacteria and viruses. The remaining 45% percent of blood includes red blood cells, platelets, and white blood cells, referred to herein as the "cellular element." While UBI has had some success, one disadvantage is that UV light may damage some parts of the cellular element, such as red and white blood cells.

UV light will not damage blood plasma alone, however. Plasmapheresis is the process of removing and replacing a patient's blood plasma. The process is also referred to as plasma exchange or therapeutic plasma exchange (TPE). TPE is commonly used as a treatment for autoimmune disorders. A related procedure is continuous veno-venous hemofiltration (CVVH). CVVH is a short term treatment used with patients with acute or chronic renal failure who cannot tolerate hemodialysis. With CVVH, blood is taken from the patient and guided into a CVVH machine or dialyzer, where it is filtered and waste fluid is removed. Fluids and electrolytes are then replaced before the blood is returned to the patient.

To date, TPE and UBI have not been successfully combined. Therefore there is a need to combine TPE and UBI so as to irradiate blood plasma alone, thereby destroying viruses and bacteria therein.

SUMMARY OF THE INVENTION

The present invention is a UV box and systems and methods for irradiating plasma.

In its most basic form, the UV box includes a housing; a top with a top interior and a top exterior; a bottom with a bottom interior and a bottom exterior; a plasma diffuser disposed within the bottom interior; and at least one UV light source disposed within the top interior. The housing is capable of being in an open position or a closed position. The top and the bottom of the housing are sized and configured such that the top interior and the bottom interior face one another when the housing is in the closed position. The plasma diffuser has a plasma inlet through which plasma enters the plasma diffuser and a plasma outlet through which the irradiated plasma exits the plasma diffuser. When the housing is in the closed position, the respective dispositions of the at least one UV light source in the top interior and the plasma diffuser in the bottom interior are such that the plasma diffuser and the plasma therein are exposed to UV radiation from the UV light source.

The UV box may be advantageously used in conjunction with a dialysis machine, a plasmapheresis machine, a CVVH, or similar machines by being connected to these machines. The UV box may also be integrated with any of these machines. As each of these machines involves filtering, replacing, or otherwise treating blood, they are referred to collectively herein as "blood cleaning machines." As used herein, when it is said that the UV box is "connected" to the blood cleaning machine, it means that the UV box is not integrated into the blood cleaning machine, but rather has been connected to the blood cleaning machine as an addon. As used herein, when it is said that the UV box is "integrated" into the blood cleaning machine, it means that the blood cleaning machine was originally constructed with the UV box already incorporated into the machine.

The housing of the UV box may be any housing appropriately sized to accommodate the UV light source and the plasma diffuser in appropriate positions relative to one another, and that will not be damaged from UV light from the UV light source. The housing is preferably opaque so as to block the UV radiation being emitted from the UV light source when the UV box is in use. In some embodiments the top interior and/or bottom interior of the housing is lined with aluminum or another material that reflects UV light, so as to provide additional focused irradiation from the UV light source disposed therein. It is understood that when the UV box is incorporated into a blood cleaning machine, the top and bottom of the housing may be part of the larger blood cleaning machine.

The housing preferably includes means for adjusting the housing between the open and closed positions. The adjusting means are preferably at least one hinge between the top and bottom of the housing, but may be snaps or other closures commonly used in the art. In some embodiments, the top merely rests on the bottom when the housing is in the closed position and is placed aside when the housing is in the open position. In such embodiments, no means for adjusting between the positions is required. In addition, when the UV box is incorporated within a blood cleaning machine, the housing is likely in a set position and may not even be easily accessible from the exterior of the blood cleaning machine. The housing preferably includes means for locking in a specific plasma diffuser, such as a specific configuration of a plasma diffuser, so that that housing may only be used with that plasma diffuser. This may ensure accurate UV exposure to the plasma flowing therethrough.

As discussed herein, the UV light source is designated as being disposed in the top of the housing and the plasma diffuser in the bottom of the housing, but it is understood that these top and bottom designations are arbitrary. The designations as written are likely preferably, however. The top of the housing will be slightly raised above the bottom, so gravity may aid in encouraging the plasma through the lower bottom portion. Also, in practice, whichever section holds the plasma diffuser will be attached on either side of the plasma inlet and plasma outlet to tubes. As such, it may be easier for the bottom to hold the plasma diffuser and remain relatively stationary, while the untethered top portion is moved to adjust the housing between the open and closed positions. That said, the UV box would still function if the plasma diffuser were disposed in the top interior of the housing and the UV light source were disposed in the bottom interior. As such, it is understood that these designations may be reversed and the reverse designation is also considered to be within the scope of the invention.

The purpose of the plasma diffuser is at least twofold—first, to slow the flow of the plasma through the plasma diffuser, so that the plasma has more time exposed to the UV light, and second, to provide a relatively large surface area for the plasma to coat, so that more of the plasma has the opportunity to be exposed to the UV light. In order for the plasma within the plasma diffuser to be exposed to the UV light, the plasma diffuser must be at least translucent and preferably transparent and should not include any material that would act as UV radiation shielding. Two preferred plasma diffusers are the "maze configuration" and "funnel configuration" plasma diffusers. As used herein, the "maze configuration" plasma diffuser is a plasma diffuser that requires the plasma to travel back and forth horizontally through a series of hairpin-like turns, as the plasma travels vertically between the plasma inlet at one end of the vertical length to the plasma outlet at the other end of the vertical length. (It is understood that "horizontal" and "vertical" are arbitrary in that description.) As used herein, the "funnel configuration" plasma diffuser is shaped like a funnel with the plasma inlet at the small end of the funnel and the plasma outlet at the wide end of the funnel. As the plasma travels through the funnel configuration plasma diffuser, it will spread out over the widening inner surface of the funnel.

The plasma diffuser may be different shapes and sizes to allow for different exposure times at different blood pump speeds. Parts of the plasma diffuser that do not directly face the UV light source, such as the bottom of the plasma diffuser, closest to the bottom interior of the housing, may include a coating or surface that reflects UV light, thereby adding intensity to the UV light being exposed to the plasma when the coating or surface can catch the reflection. The plasma diffuser may be any medium that carries the plasma and allows the plasma to be exposed to UV light. As such, the plasma diffuser may be as simple as a tube or a beaker. The preferred embodiments, such as the maze and funnel configurations, may be adjusted to calibrate the dosage of UV exposure, which may not be possible with such simpler configurations of the plasma diffuser. In some embodiments, the aperture of the plasma diffuser through which the plasma flows may be mechanically narrowed or widened to vary flow speed and exposure. Such variations to the plasma diffuser operation, such as adjusting to calibrate for UV exposure or changing the aperture width, may be performed based on what is known about the particular pathogen being targeted or the pathogen load, for examples.

The at least one UV light source is preferably two or three UV light sources, each emitting UV radiation with a different wavelength. When the at least one UV light source is first and second UV light sources, they emit first and second wavelengths that are preferably 265 and 280 nm, respectively. A third UV light source with a third, different wavelength may also be included. More than three UV light sources may be included. When two UV light sources are included, they may each emit the same wavelength. When two or more UV light sources are included, the wavelengths emitted by each light source need not be distinct. Some embodiments may include a UV light source tailored to the pathogen being targeted by the treatment. If evidence shows that a certain pathogen is more readily inactivated by a specific wavelength, for example, then a specific UV light source emitting that wavelength may be used. The pathogen may also dictate whether one UV light source or two or three combined UV light sources are used.

There are three main configurations of the system of the present invention. In its most basic form, the first configuration of the system of the present invention includes a blood outlet tube extending between a patient's vein and a plasma separator; the plasma separator that separates blood into plasma and a cellular element; a blood pump that pumps blood through the blood outlet tube and into the plasma separator; means for exposing the plasma to UV radiation (hereinafter "exposing means") that include at least a plasma vessel with a plasma inlet and a plasma outlet and at least one UV light source; a plasma inlet tube extending between the plasma separator and the exposing means; a blood inlet tube extending back to the patient's vein; a plasma outlet tube extending between the exposing means and the blood inlet tube; and a cellular element tube extending between the plasma separator and the blood inlet tube.

While the second and third configurations of the system of the present invention have their advantages, the first configuration may be preferable because of its simplicity. The more components are added to the system, as in the second and third configurations, the more likely that the system may clog. On the other hand, in the first configuration, all of the patient's plasma is exposed to UV radiation, which will kill pathogens, but may also damage useful proteins. The second configuration, while more complex than the first, separates the plasma so that those useful proteins are not exposed to UV radiation. The first configuration of the system of the present invention may a blood cleaning machine that is a CVVH machine or a hemodialysis machine with an integrated or connected UV light box of the present invention. The second configuration of the system of the present invention may be a blood cleaning machine that is a plasmapheresis machine that can handle two dialyzers with an integrated or connected UV light box of the present invention. The third configuration of the system of the present invention may be a blood cleaning machine that is a plasmapheresis machine and a CVVH machine with an integrated or connect UV light box of the present invention.

In practice, the system preferably begins and ends at a vein of a patient. The blood outlet tube extends between an outlet arm end at the patient's vein and a separator end at the plasma separator. The vein is preferably either in the arm or the neck. References to the outlet arm end and later to the inlet arm end, as well as to the patient's arm generally, are understood to not necessarily refer to the patient's arm, but to anywhere where the vein is located. It is preferred that the system include removing intravenous (IV) equipment installed at the outlet arm end of the blood outlet tube. As used herein, the "removing IV equipment" includes a needle with catheter and tubing or a surgically inserted catheter, such as a double lumen catheter. A double lumen catheter is preferred when the vein is in the neck. The blood pump pumps blood through the blood outlet tube and encourages the blood toward the plasma separator. The blood pump may be any commonly used in the art. It is preferred that the system also include an anticoagulant infusion pump disposed just before the plasma separator, although it may be disposed anywhere on the blood outlet tube. The anticoagulant infusion pump pumps an anticoagulant, such as a heparin or a citrate dextrose solution (commonly referred to simply as "citrate"). The inclusion of anticoagulant will prevent the blood from clotting. The plasma separator separates the blood into plasma and the cellular element. The cellular element leaves the plasma separator through the cellular element tube, which extends between the plasma separator and a joint end. The plasma leaves the plasma separator through the plasma inlet tube and travels through the plasma inlet into the plasma vessel of the exposing means. It is understood that both the plasma separator and the plasma component separator (discussed below with reference to the second and third configurations of the system of the present invention) are specific types of dialyzers.

The exposing means may be any variation of the UV box of present invention, as described above. It is preferred that the plasma vessel of the exposing means be a plasma diffuser, as described above. Many specific references to plasma diffusers herein are understood to be generalizable to plasma vessels other than plasma diffusers. As with the more specific plasma diffuser, the plasma vessel has at least a twofold purpose—first, to slow the flow of the plasma through the plasma diffuser, so that the plasma has more time exposed to the UV light, and second, to provide a relatively large surface area for the plasma to coat, so that more of the plasma has the opportunity to be exposed to the UV light. It is understood that these purposes and structures necessary to achieve them are inherent to plasma vessels and plasma diffusers. As such, these purposes and structures should be considered to be part of the terms "plasma vessel" and "plasma diffuser" as used herein. The exposing means may also be only a plasma vessel, such as a plasma diffuser, and a UV light source, without the housing of the UV box, however. The UV box is preferred because it protects system users and patients from the UV radiation and focuses the UV radiation on the plasma diffuser. In very simple setups of the system of the present invention, however, only the key components of the plasma diffuser and the UV light source are necessary. A basic UV lamp could be directed toward the plasma diffuser as the plasma travels through the plasma diffuser, for example. In any embodiment of the exposing means, however, the plasma diffuser and the at least one UV light source may be any of the variations discussed above with respect to the UV box of the present invention, such as maze or funnel configurations for the plasma diffuser and multiple UV light sources with various wavelengths for the UV light source. The plasma therefore enters the exposing means by way of the plasma inlet of the plasma vessel and leaves the exposing means by way of the plasma outlet. Plasma that has gone through the exposing means and been irradiated by the UV light source is called "irradiated plasma" herein.

The irradiated plasma then travels through the plasma outlet tube, which ends at the joint end of the cellular element tube. The irradiated plasma and cellular element are now reunited as treated blood. The treated blood then travels through the blood inlet tube, which extends between the joint end and an inlet arm end. The inlet arm end ends back at the patient's arm. As with the outlet arm end of the blood outlet tube, it is preferred that the system also include replacing IV equipment installed at the inlet arm end of the blood inlet tube. As used herein, the "replacing IV equipment" includes a needle or the venous end of a double lumen catheter.

It is preferred that the system also include a system interface. The system interface includes at least a power switch for the system and at least one monitor of a patient condition. The power switch may be systemwide, and turn on and off all powered system components, such as pumps, valves, and the UV light source. The power switch may also include separate switches to turn on the various components individually. The at least one monitor of a patient condition may display, for examples, the patient's venous pressure, arterial pressure, volume of blood drawn, blood temperature, etc. The at least one monitor may also be an air detector to prevent any injection of air into the patient. Basic vital signs, such as blood pressure, pulse, and oxygen may also be monitored and displayed. In preferred embodiments, the system interface may include at least one alarm that indicates if a patient condition is outside of a preferred range. The alarm might indicate if a patient's venous pressure has dropped dangerously low, for example. One of at least ordinary skill in the art will recognize there may be a variety of useful alarms included in the system interface, and each of these alarms is considered to be within the scope of the present invention.

In preferred embodiments, the system interface may also include at least one user setting. As used herein, "user setting" means any setting that may be adjusted or receive input from a user regarding how aspects of the system will operate. System operations that may be varied by a user may include the volume of blood drawn from the patient; the pump speed; or the wavelength of the UV light source. A user setting may allow adjustment of alarm ranges, defining ranges of various metrics that are acceptable versus when an alarm will initiate. An alarm may be programmed to warn of pressure changes, blood clotting, or escape of air in the system, for examples. A user setting may also allow for presets of a specific combination of operation parameters or for a specific single operation parameter. Through experimentation, it may be discovered that certain system operations parameters may be more effective against specific pathogens, for example. A user setting may be a preset that encompasses this optimal set of parameters to address that pathogen. One of at least ordinary skill in the art will recognize that there may be a variety of useful user settings included in the system interface, and each of these user settings is considered to be within the scope of the present invention.

Preferred versions of the first configuration also include a flow control module and a waste deposit disposed on the plasma outlet tube. The flow control module only allows a first percentage of the irradiated plasma to reunite with the cellular element. A second portion of the irradiated plasma is deposited in the waste deposit. This helps control the viral load, albeit inactivated, that is returned to the patient. In addition, it can tailor what is returned to the patient based on what pathogen the system is treating. If the pathogen is a virus, for example, it may be preferable to only return the inactivated virus to the patient at a rate that will facilitate smooth antibody production, while removing significant viral load. If the targeted pathogen is a bacterial agent, it may be preferable to return only a small portion of inactivated bacteria to trigger the immune response, while avoiding the risk of developing reactions from endotoxins that may result from the dead bacteria. Endotoxins are toxins present inside a bacterial cell and are released when the cell disintegrates. Endotoxins can cause severe symptoms depending on the kind of bacteria. It is understood that the blood may contain a one or more viruses and/or one or more bacteria and the system can handle multiple pathogens at the same time. It is preferred that the waste deposit include a waste valve that controls a flow of the second remaining percentage of the irradiated plasma. Essentially, the waste valve functions to open the waste deposit when it is time for it to accept the second remaining percentage and closes the waste deposit after the second portion has been deposited so that it cannot remix with the first percentage. The waste valve may be fully opened, fully closed, or may be adjustable to allow for a specific percentage to go to waste. In such embodiments that include the flow control module and waste deposit, some plasma is not returned to the patient so it is preferable to also include an intravenous fluid replacement device.

In its most basic form, the second configuration of the system of the present invention includes any form of the first configuration of the system as described above, and a plasma component separator, a plasma pump, and a small plasma tube.

The plasma component separator is disposed between the plasma separator and the plasma diffuser of the exposing means. Any plasma component separator commonly used in the art may be used. While the terms "plasma separator" and "plasma component separator" are similar and both used herein, it is understood that they are distinct devices with distinct functions. Specifically, the plasma separator separates blood into plasma and the cellular component. The plasma component separator separates the plasma into small plasma and large plasma. The small plasma with its valuable proteins is not sent on to irradiation, thus protecting those valuable proteins. The small plasma tube extends from the plasma component separator to intersect with the cellular element tube. The small plasma rejoins the cellular element at the junction of the small plasma tube and the cellular element tube. The plasma component separator divides the plasma inlet tube into a first section extending between the plasma separator and the plasma component separator and a second section extending between the plasma component separator and the plasma vessel of the exposing means.

Plasma travels through the first section of the plasma inlet tube to arrive at the plasma component separator. A plasma pump pumps the plasma through this first section. Only large plasma then travels through the second section of the plasma inlet tube to the exposing means. In this way, only the large plasma, which houses the microbes will be irradiated by the exposing means. The small plasma has been diverted away to rejoin the cellular element. The irradiated large plasma then travels through the plasma outlet tube, which intersects with the cellular element tube at the joint end. At this point, the irradiated large plasma is reunited with the small plasma and the cellular element. The combined treated blood travels back to the patient through the blood inlet tube.

Preferred versions of the second configuration also include a flow control module and a waste deposit disposed on the plasma outlet tube. The flow control module allows a controlled portion that is a first percentage of the irradiated large plasma to reunite with the cellular element and the small plasma. The discarded remaining percentage of the irradiated plasma is deposited in the waste deposit. It is preferred that the waste deposit include a waste valve. Essentially, the waste valve functions to open the waste deposit when it is time for it to accept the discarded remaining percentage, which is measured so as to know the volume of the discarded remaining percentage.

In its most basic form, the third configuration of the system of the present invention includes any form of the second configuration of the system as described above and a CVVH dialyzer, likely provided in the form of a CVVH machine. The third configuration of the system adds aspects of CVVH thus providing double filtration plasmapheresis UV therapy with CVVH capability. This configuration may be used for the critical patient who develops kidney failure or fluid overload. This combines two procedures in a single system or machine.

The dialyzer is any commonly used in the art of CVVH or as a part of a CVVH machine. As mentioned above, although both the plasma separator and plasma component separator are types of dialyzers, it is understood that as used herein, "dialyzer" is referring specifically to a dialyzer of the type commonly used with CVVH. Standard dialyzers include at least a bubble detector and venous and arterial pressure monitors. The third configuration also preferably includes a dialyzer inlet tube, a dialyzer valve, a dialyzer pump, a dialyzer outlet tube, and a bypass valve. After the large plasma has been irradiated and reunited with the cellular element and small plasma, it flows on to the dialyzer for fluid removal and a form of dialysis. An intravenous fluid replacement device is preferably included in the third configuration. The dialyzer valve and bypass valve may act to totally isolate the CVVH components from the components of the second configuration of the system, so that the third configuration acts identically to the second configuration. When necessary, however, they may act to send the reunited blood to the dialyzer for further treatment before being returned to the patient, with some fluid replacement by the fluid replacement device if needed.

In its most basic form, the method of the present invention comprises the steps of removing blood from a patient; separating the blood into plasma and a cellular element; exposing at least a portion of the plasma to at least one UV light source; reuniting at least a portion of the irradiated plasma with the cellular element; and replacing the treated blood into the patient. The treated blood will contain inactive or dead pathogens that can facilitate the formation of different kinds of antibodies. This allows the body to fight the infection as though it has a customized or individual vaccine or treatment for that specific patient. As such, the method is performed on a single patient. Notably, the systems and method of the present invention may be used for such customized treatment for viral and bacterial agents, as well as for venoms by using the same process to denature and inactivate venom proteins.

The step of exposing at least a portion of the plasma to UV radiation allows for embodiments of the method of the present invention using an embodiment of the system of the present invention that includes a plasma component separator, where only the large plasma portion of the plasma is exposed to the UV radiation. It is understood, however, that when the method of the present invention is performed using an embodiment of the system of the present invention that does not include a plasma component separator, all of the plasma may be exposed to the UV radiation. The step of reuniting at least a portion of the irradiated plasma with the cellular element allows for embodiments of the method of the present invention using an embodiment of the system of the present invention that includes the flow control module and the waste deposit, where a percentage of the irradiated large plasma is deposited into the waste deposit, rather than reunited with the cellular element. It is understood, however, that when the method of the present invention is performed using a system of the present invention that does not include the flow control module or waste deposit, all of the irradiated plasma may be reunited with the cellular element.

The step of removing the blood from the patient is performed by any means commonly used in the art, preferably IV venipuncture using removing IV equipment or a double lumen catheter. It is preferred that the method of the present invention be performed through a continuous loop at the patient's location, i.e. that blood is drawn from the patient, taken through a series of tubes and components, as described herein, and replaced into the patient, all through a single system of the present invention. In some embodiments, however, the blood may be drawn and treated separately, not necessarily at the exact location of the patient. In such embodiments, the blood is then transfused back into the patient after being treated through the method of the present invention.

The step of separating the blood into plasma and a cellular element is performed by running the blood through a plasma separator. The step of exposing the plasma to at least one UV light source is preferably performed by sending the plasma through a plasma vessel, such as a plasma diffuser, that is positioned proximate to at least one UV light source such that the at least one UV light source emits UV radiation onto the plasma vessel. When the plasma vessel is a plasma diffuser, the step of sending the plasma through a plasma diffuser preferably comprises the step of sending the plasma through a maze configuration plasma diffuser or a funnel configuration plasma diffuser. The at least one UV light source may be one, two, or three light sources, each of which may emit different wavelengths of UV radiation. In some embodiments, the step of exposing the plasma to at least one UV light source may include exposing the plasma to UV light for a specified amount of time. It may be determined, for example, that the plasma includes an unusually large pathogen load that will require additional exposure to the UV light. Alternatively, experimentation may have shown that a specific pathogen is needs more or less exposure for inactivation. There also may be time variations based on whether it is desirable or necessary to inactivate the pathogen only or to fully kill the pathogen.

The step of sending the plasma through a plasma vessel that is positioned proximate to at the at least one UV light source may comprise sending the plasma through a UV light box of the present invention. The steps of sending the plasma through a UV light box are implied by the discussion of the UV light box of the present invention, as discussed above. These steps include disposing at least one UV light source in the top of the housing; disposing the plasma diffuser in the bottom of the housing; mating the top and bottom of the housing so that the UV light source and the plasma diffuser face one another; activating the UV light source; and sending the plasma through the plasma diffuser. As a point of clarification, as used herein, when it is said that blood is being sent through a tube, it is understood that the blood is running through the tube or being diverted through it or traveling through it and that there is directional flow of the blood, sometimes assisted by a pump. These steps are also considered to be a separate UV box method of their own.

The step of reuniting the irradiated plasma with the cellular element preferably includes the steps of sending the cellular element from the plasma separator, through a cellular element tube that ends in a joint end; sending the irradiated plasma from the plasma diffuser, through a plasma outlet tube that also ends in the joint end; and sending both the cellular element and the irradiated plasma through a blood inlet tube.

The step of replacing the treated blood into the patient is performed by any means commonly used in the art, preferably by IV venipuncture using replacing IV equipment. It is preferred that the blood inlet tube extend between the joint end and terminate in the IV equipment and that the step of replacing the treated blood include sending the treated blood through the blood inlet tube.

Preferred embodiments of the method of the present invention also include the following step: after the step of removing blood through IV venipuncture and before separating the blood, pumping the blood into the plasma separator. Preferred embodiments may also include the step of pumping anticoagulant into the blood with an anticoagulant infusion pump. Preferred embodiments may also include the steps of determining a desired UV exposure level and selecting the size and configuration of the plasma vessel so as to achieve the desired UV exposure level. As noted above, the plasma vessel may take many forms so long as the plasma vessel slows down the flow of the plasma and provides surface area on which the plasma will be exposed to the UV light source. Different configurations and sizes of the plasma vessel may vary the exposure level to UV. Preferred embodiments may also include the step of replacing fluid into the treated blood. Preferred embodiments may also include the steps of allowing only a first percentage of the irradiated plasma to reunite with the cellular element; and disposing of the remainder of the irradiated plasma. Even though the virus, bacteria, or venom will have been inactivated through the irradiation, controlling how much of the inactivated pathogen returns to the patient will help to decrease the pathogen load.

When the method of the present invention is performed using the second or third configuration of the systems of the present invention, discussed above, additional steps are included. After the step of separating the blood, the method also includes the steps of separating the plasma into small plasma and large plasma; sending only the large plasma on to the step of exposing the plasma to UV radiation; and reuniting the small plasma with the cellular element. Preferred embodiments also include the steps of allowing only a first percentage of the irradiated large plasma to reunite with the cellular element; and disposing of the remaining percentage of the irradiated large plasma. With the third configuration of the system of the present invention, the method also includes the steps of sending the treated blood through a dialyzer for dialysis and/or fluid removal.

These aspects of the present invention are not meant to be exclusive and other features, aspects, and advantages of the present invention will be readily apparent to those of ordinary skill in the art when read in conjunction with the following description and accompanying drawings.

DETAILED DESCRIPTION

Figure 1A:
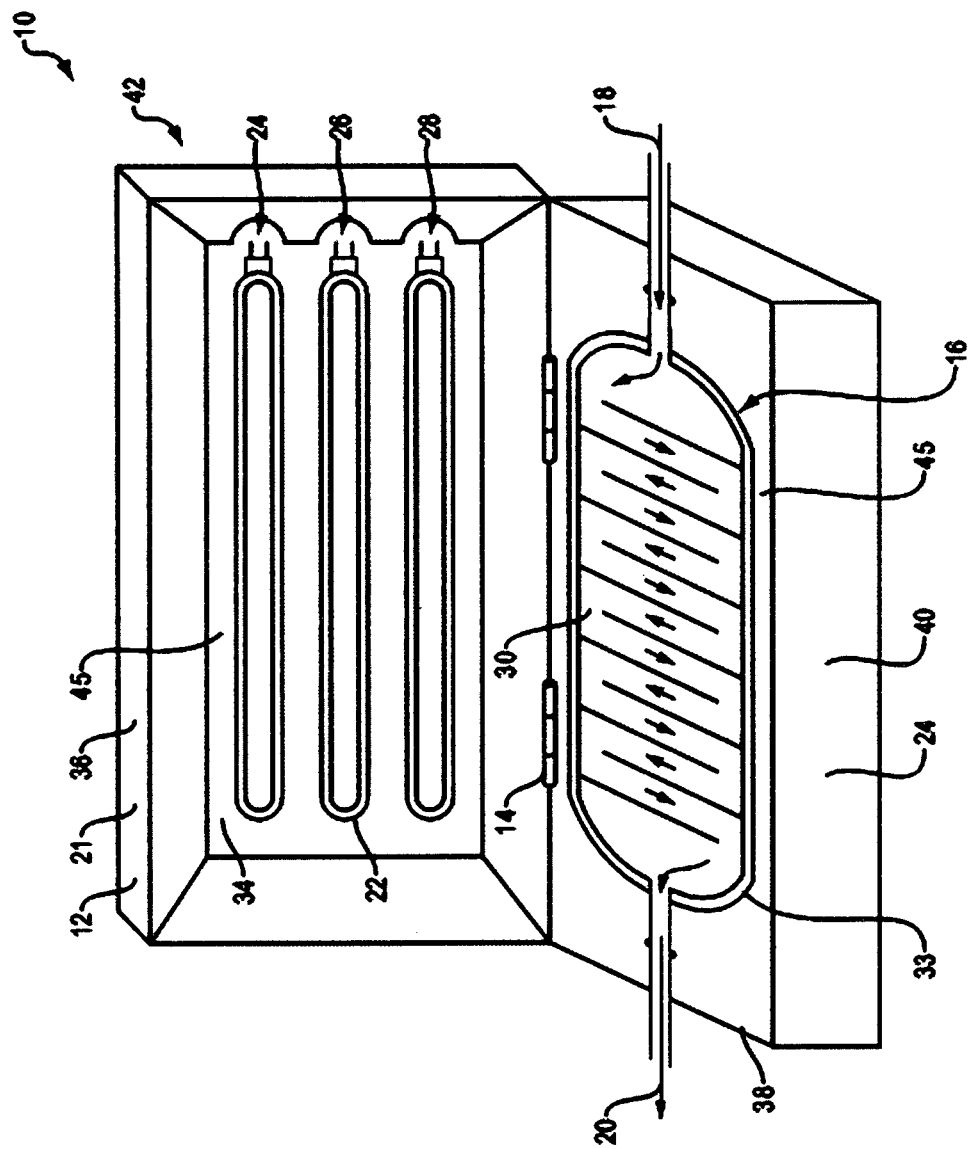
FIG. 1*a* is a perspective view of the UV box of the present invention in the open position.

Referring first to FIG. 1a, a perspective view of UV box 10 of the present invention in open position 42 is provided. UV box 10 includes housing 12, top 21, bottom 24, and means for adjusting between the open and closed positions 14. Means 14 are preferably at least one hinge. Top 21 and bottom 24 are sized so that they align with one another when housing 10 is in the closed position 44 (shown in FIG. 1b). Top 21 includes top interior 34 and top exterior 36. Bottom 24 includes bottom interior 38 and bottom exterior 40. Top interior 34 and bottom interior 38 face one another when housing 12 is in the closed position. UV light source 22 is disposed within top interior 34. Plasma diffuser 16 is disposed within bottom interior 38. When housing 12 is in the closed position and UV light source 22 is activated, UV light source 22 will irradiate plasma diffuser 16 and the plasma therein. As shown, UV light source 22 includes first, second, and third UV light sources 24, 26, 28, each of which emits a different wavelength of UV radiation. Plasma diffuser 16 includes plasma inlet 18 through which plasma to be treated is introduced into plasma diffuser 16, and plasma outlet 20, through which irradiated plasma leaves plasma diffuser 16. Plasma diffuser 16 is shown in maze configuration 30. It is understood that funnel configuration 32, as shown in FIG. 2b, or any other plasma diffuser may be substituted. Locking means 33 for locking in a specific plasma diffuser 16 may include shaping bottom interior 38 so that only the specific plasma diffuser 16 will fit into UV box 10. Top interior 34 and bottom interior 38 include UV reflective coating 45, such as aluminum. Although not shown, it is understood that the portion of the plasma diffuser 16 that faces toward the bottom interior 38 and away from the UV light source 22 may also include such a UV reflective coating 45. As used herein, when "a portion of the plasma diffuser" is referenced, it is understood that it is the portion as described above.

Figure 1B:
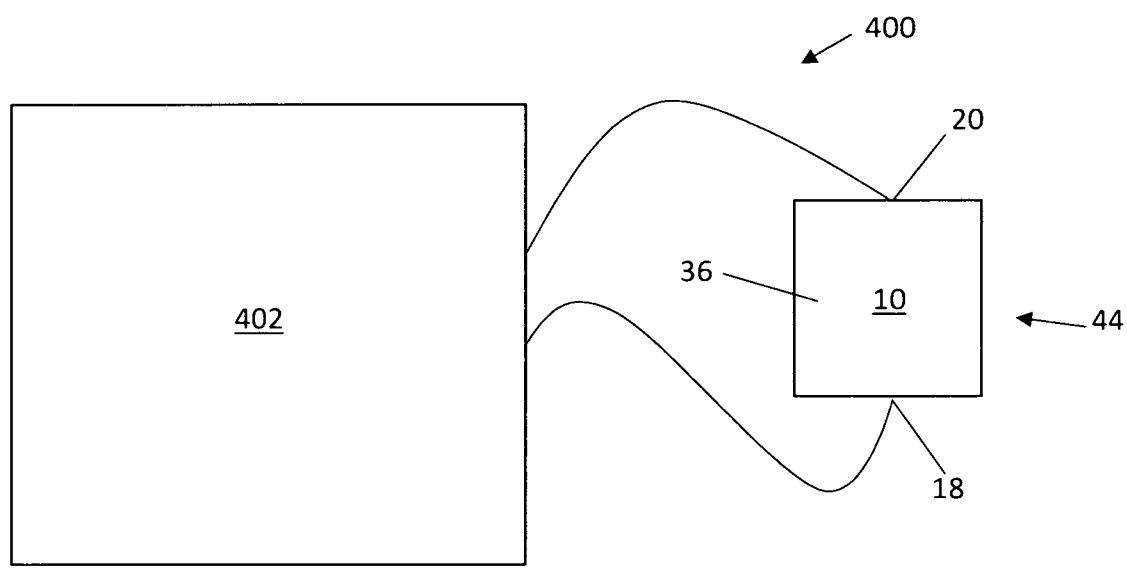
FIG. 1b is a diagram of a blood cleaning machine of the present invention with UV box connected thereto.

Now referring to FIG. 1b, a diagram of blood cleaning machine 400 of the present invention is provided. Blood cleaning machine 400 includes a machine 402 that cleans, filters, or replaces blood, such as a CVVH machine, a dialysis machine, or a plasmapheresis machine. This machine 402 is shown connected to UV box 10. UV box 10 is in closed position 44, so that only top exterior 36 is visible from this view. The connection between machine 402 includes at least tubing extending between machine 402 and plasma inlet 18 and tubing extending between plasma outlet 20 and machine 402. It is understood that in some embodiments of blood cleaning machine 400, UV box 10 is incorporated into the machine 402 and is therefore not necessarily visible from the exterior of machine 402.

Figure 2A:
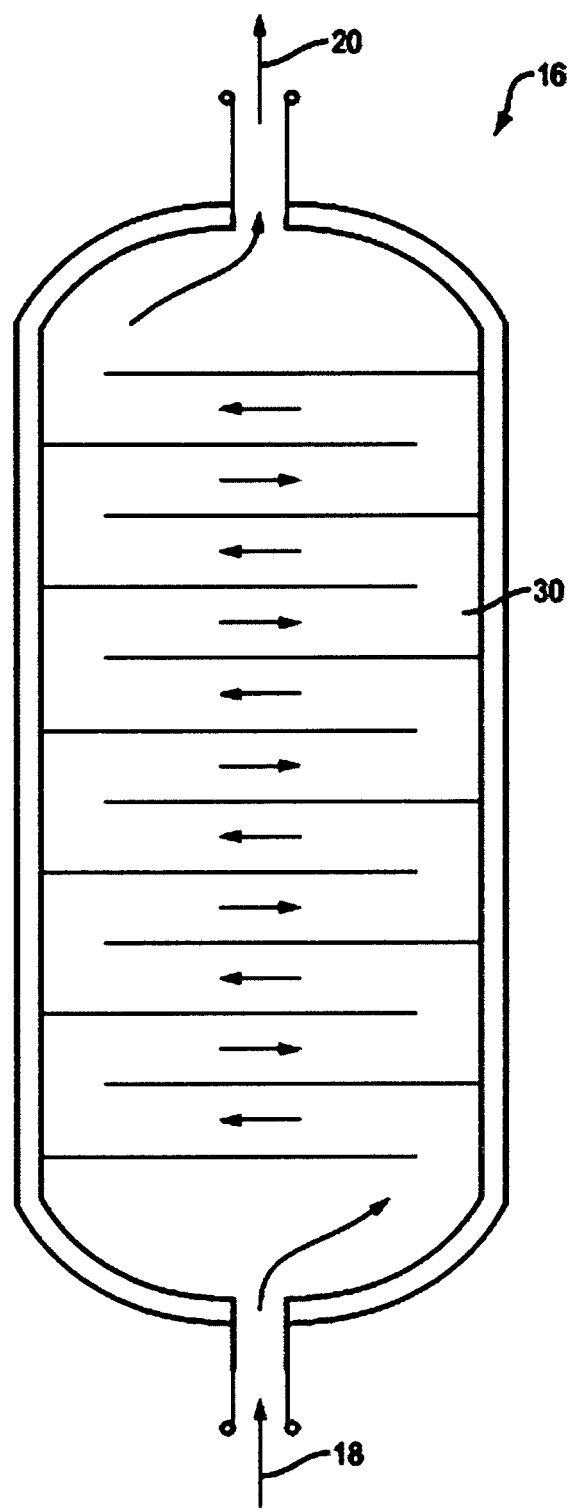
FIG. 2a is a diagram of a plasma diffuser in the maze configuration.
Figure 2B:
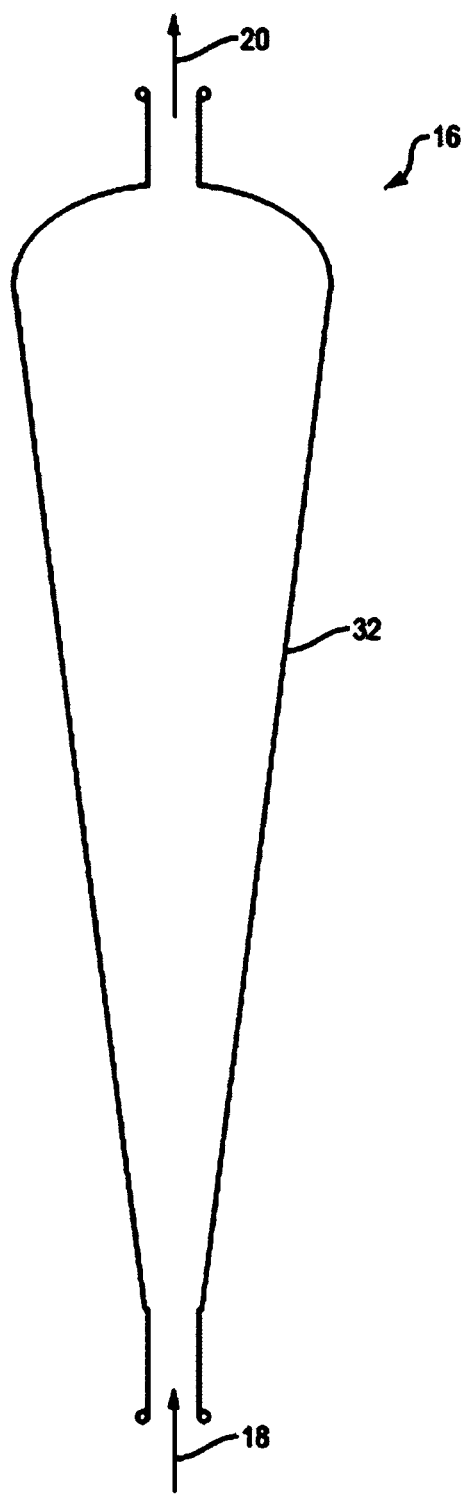
FIG. 2b is a diagram of a plasma diffuser in the funnel configuration.

Now referring to FIGS. 2a and 2b, diagrams of two preferred plasma diffusers 16, in the maze configuration 30 and the funnel configuration 32, respectively, are provided. As shown in FIG. 2a, in maze configuration 30, the plasma travels back and forth horizontally through a series of hairpin-like turns, as the plasma travels vertically between plasma inlet 18 at one end of the vertical length to plasma outlet 20 at the other end of the vertical length. (It is understood that "horizontal" and "vertical" are arbitrary in that description.) The arrows within maze configuration 30 indicate the path that the plasma must take as it travels through. As shown in FIG. 2b, funnel configuration 32 is shaped like a funnel with plasma inlet 18 at the narrow end of the funnel and plasma outlet 20 at the wide end of the funnel. As the plasma travels through funnel configuration 32, it will spread out over the widening inner surface of the funnel.

Figure 3A:
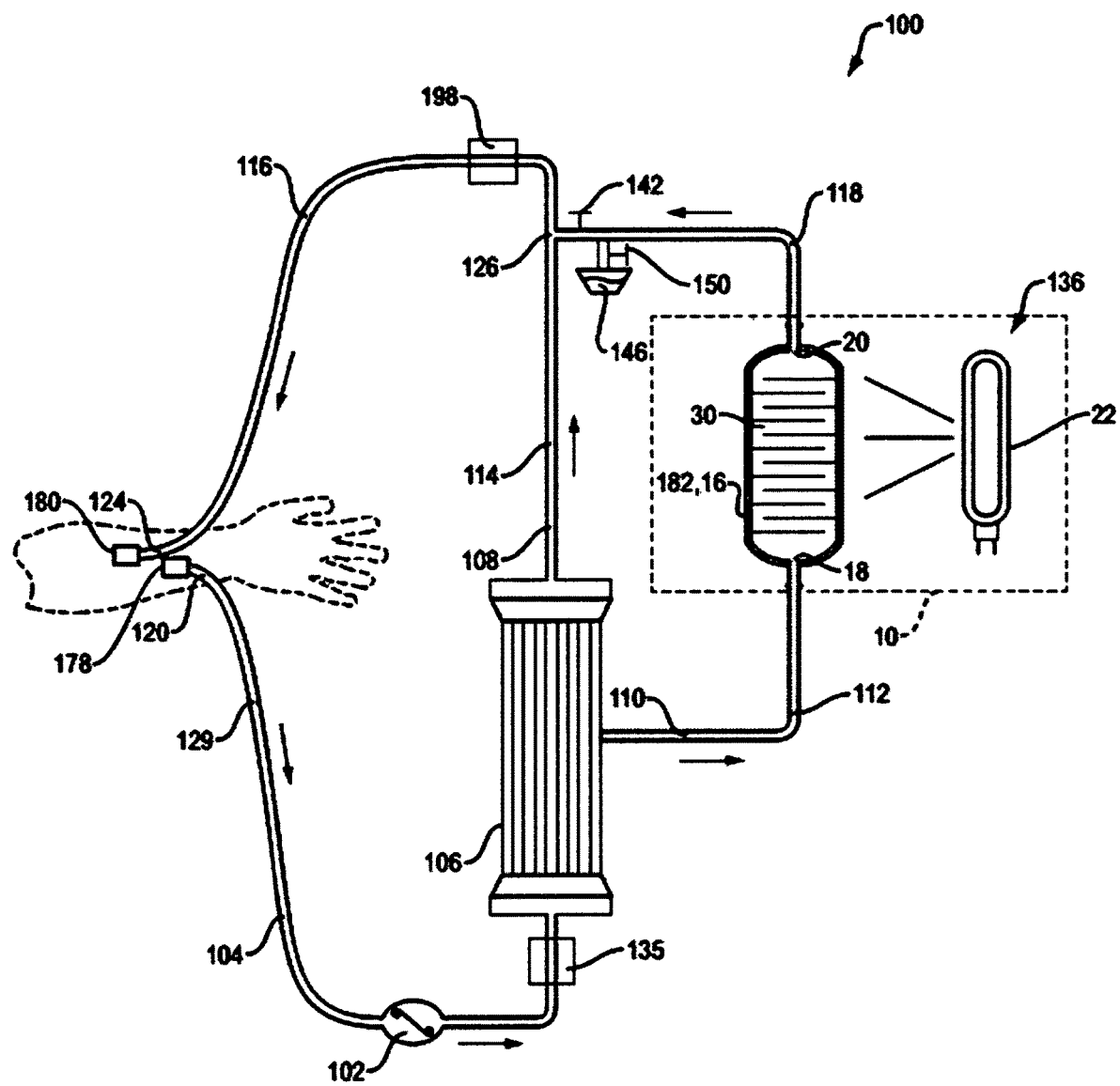
FIG. 3a is a first configuration of the system for irradiating plasma of the present invention.

Now referring to FIG. 3a, a diagram of system 100 of the present invention in its first, simplest configuration is provided. System 100 begins and ends at the patient's arm. Removing IV equipment 178 is placed into the patient's arm to draw blood 129. Removing IV equipment 178 is connected to outlet arm end 120 of blood outlet tube 104 through which blood 129 flows. This flow is aided by blood pump 102, which pumps blood 129 into plasma separator 106. Anticoagulant infusion pump 135 pumps anticoagulant, such as a heparin or a citrate dextrose solution, into blood 129. This avoids blood clotting. Plasma separator 106 separates blood 129 into plasma 110 and cellular element 108. Cellular element 108 flows through cellular element tube 114, which extends between plasma separator 106 and joint end 126. Plasma 110 flows through plasma inlet tube 112, which extends between plasma separator 106 and exposing means 136, specifically to plasma inlet 18 of plasma vessel 182, which is plasma diffuser 16. Exposing means 136 include plasma vessel 182 and UV light source 22. In some embodiments, exposing means 136 are UV box 10 of the present invention, as described above with reference to FIG. 1 and referenced here in dashed lines. Irradiated plasma leaves plasma outlet 20 of plasma diffuser 16 and flows through plasma outlet tube 118. Flow control module 142 is disposed on plasma outlet tube 118 and allows only a first percentage of the irradiated plasma through to reunite with cellular element 108. The remaining percentage is disposed of in waste deposit 146. Waste deposit 146 includes waste valve 150 to ensure that the remaining percentage of the irradiated plasma does not remix with the first percentage. Plasma outlet tube 118 intersects with cellular element tube 114 at joint end 126, where the first percentage of the irradiated plasma and cellular element 108 are reunited and then flow through blood inlet tube 116 as treated blood. Fluid replacement device 198 provides fluid replacement into blood inlet tube 116 to replace the portion of the plasma that was disposed in waste deposit 146. Blood inlet tube 116 extends between joint end 126 and inlet arm end 124. Replacing IV equipment 180 is disposed at inlet arm end 124 and replaces the treated blood into the patient.

Figure 3B:
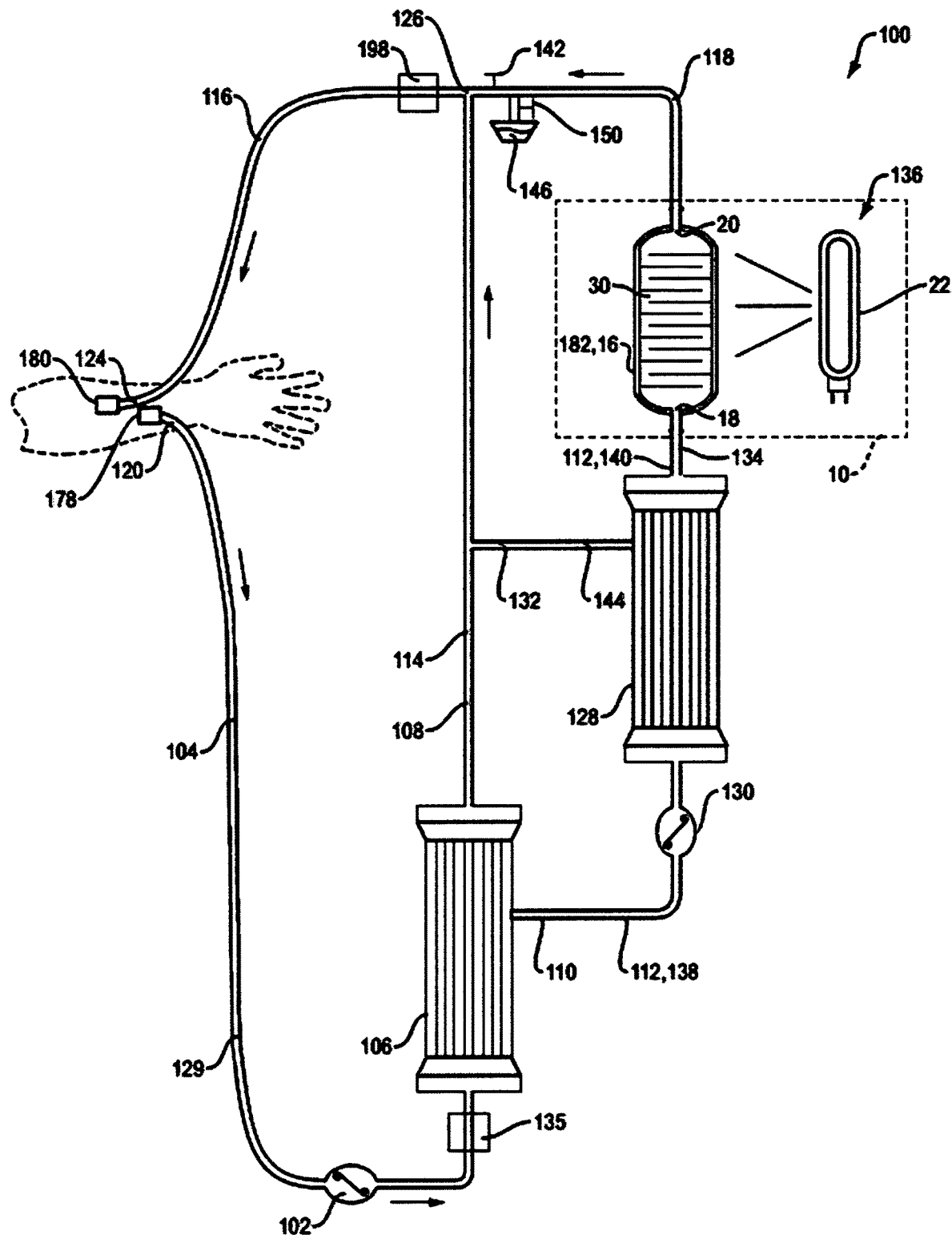
FIG. 3b is a second configuration of the system for irradiating plasma of the present invention.

Now referring to FIG. 3b, the second configuration of system 100 also includes plasma component separator 128. Plasma component separator 128 is disposed between plasma separator 106 and exposing means 136. Plasma component separator 128 divides plasma inlet tube 112 into first section 138 between plasma separator 106 and plasma component separator 128 and second section 140 between plasma component separator 128 and exposing means 136. A second pump 130 is disposed on first section 138 to aid the flow of plasma 110 into plasma component separator 128. Plasma component separator 128 separates plasma 110 into small plasma 132 and large plasma 134. Small plasma 132 travels through small plasma tube 144, which extends between plasma component separator 128 and cellular element tube 114. Small plasma 132 reunites with cellular element 108 at the intersection of small plasma tube 144 and cellular element tube 114. Large plasma 134 flows through second section 140 into exposing means 136, specifically into plasma inlet 18 of plasma vessel 182 (again shown as plasma diffuser 16 in maze configuration 30). Flow control module 142 is disposed on plasma outlet tube 118 and allows only a first percentage of the irradiated large plasma through to reunite with cellular element 108 and small plasma 132. The remaining percentage is disposed of in waste deposit 146. Waste deposit 146 includes waste valve 150 to ensure that the remaining percentage of the irradiated large plasma does not remix with the first percentage. Fluid replacement device 198 provides fluid replacement into blood inlet tube 116 to replace the portion of the large plasma that was disposed in waste deposit 146.

Figure 3C:
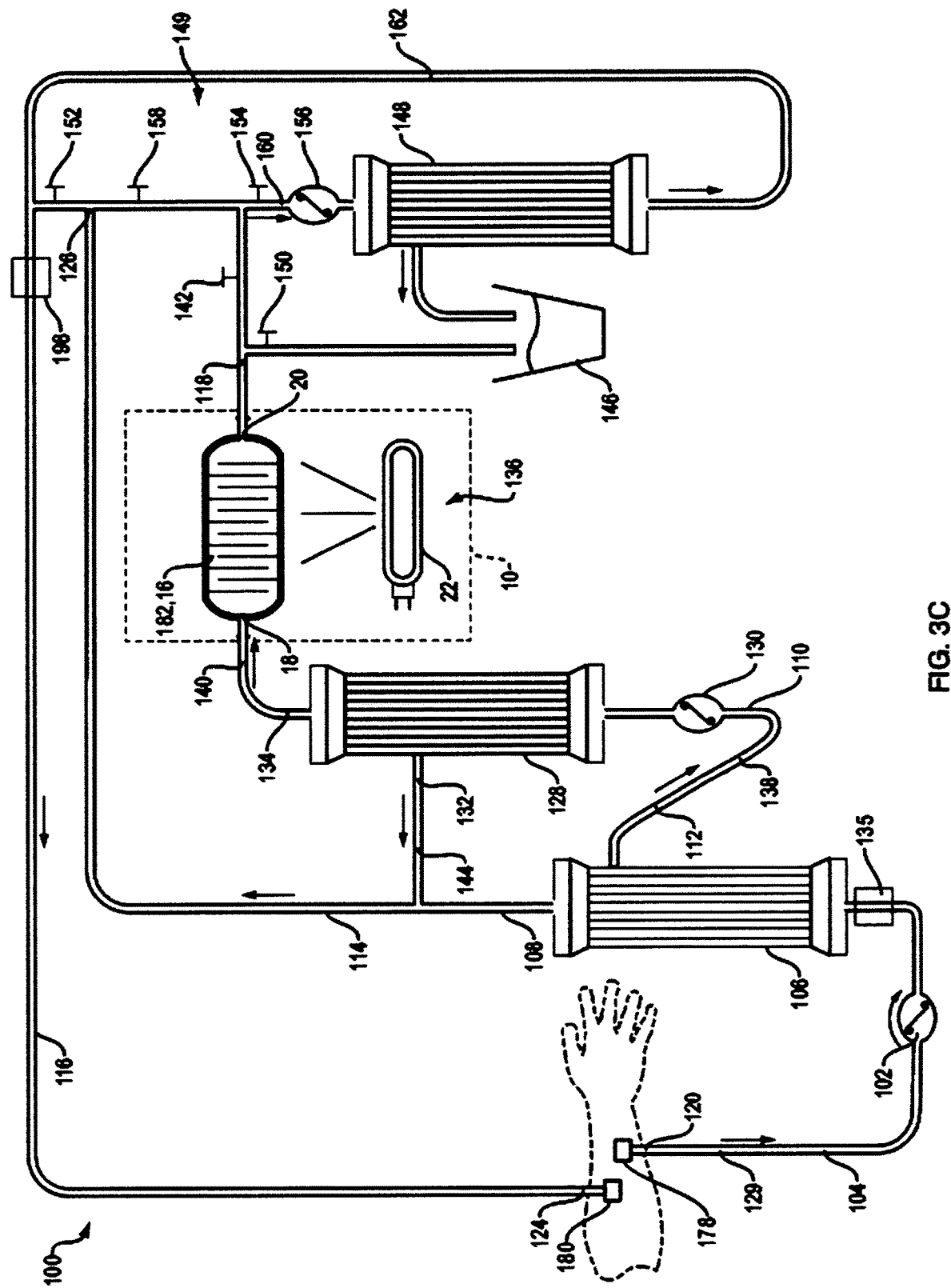
FIG. 3c is a third configuration of the system for irradiating plasma of the present invention.

Now referring to FIG. 3c, the third configuration of system 100 also includes dialyzer 148. Dialyzer inlet tube 160 extends between flow control module 142 and dialyzer 148. Dialyzer inlet tube 160 includes dialyzer valve 154. When dialyzer valve 154 is closed and bypass valve 158 and inlet valve 152 are open, the dialyzer 148 is isolated and this third configuration of system 100 acts exactly like the second configuration, shown in FIG. 3b. When inlet valve 152 is closed, and bypass valve 158 and dialyzer valve 154 are open, on the other hand, the reunited cellular element 108, small plasma 132, and irradiated large plasma 134 are pumped by dialyzer pump 156 through dialyzer 148. These series of valves and the tubing 160, 162 around dialyzer 148 that collectively may isolate the dialyzer 148 from the remainder of system 100 are referred to herein as "means for isolating the dialyzer" 149. Dialyzer 148 is connected to waste deposit 146 and deposits a portion of the dialyzed irradiated blood therein. The fully treated and dialyzed blood then travels through dialyzer outlet tube 162, which intersects with blood inlet tube 116.

Figure 4:
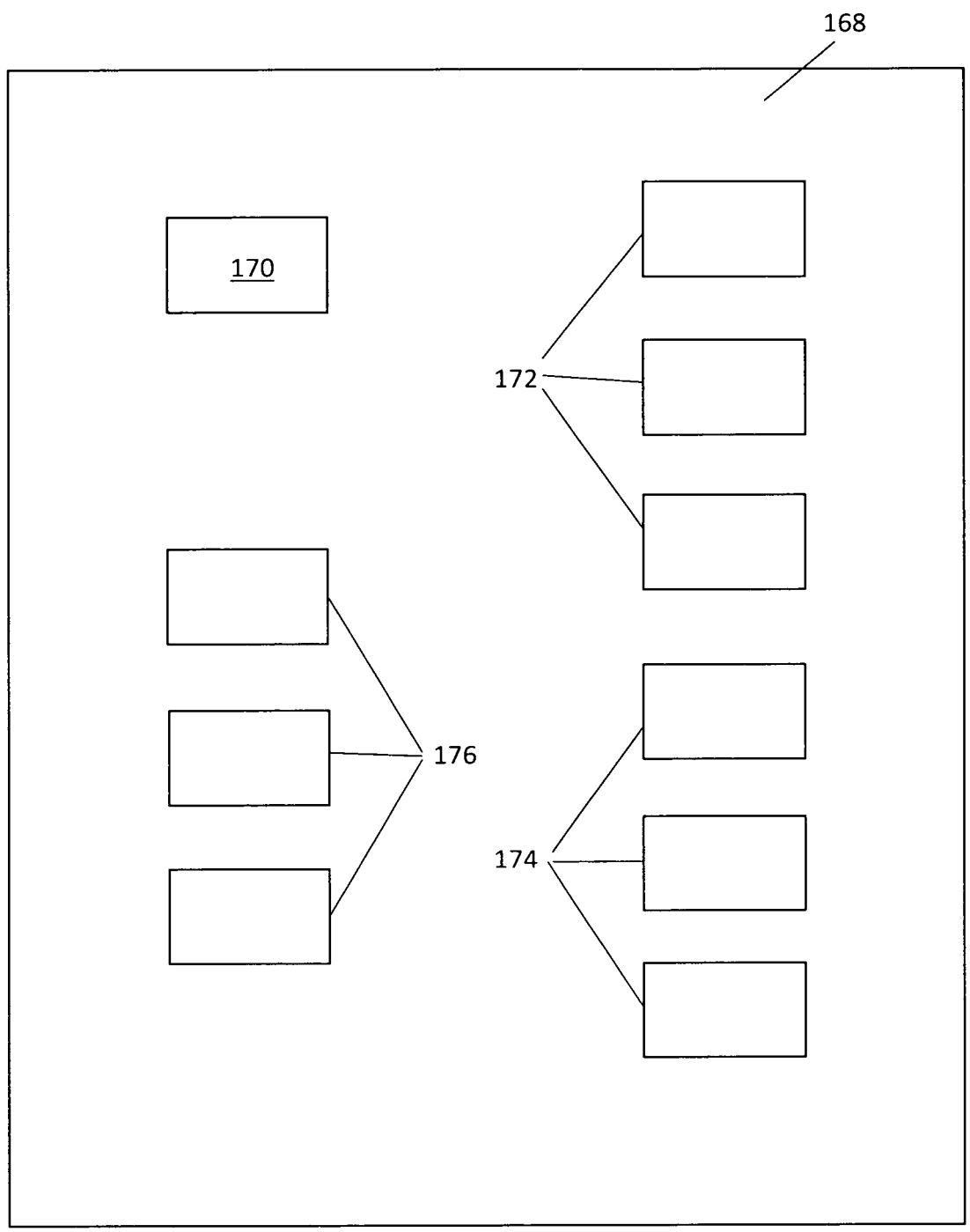
FIG. 4 is a diagram of an exemplary system interface of a system of the present invention.

Now referring to FIG. 4, a diagram of an exemplary system interface 168 of system 100 of the present invention is provided. Power switch 170 turns system 100 on and off. Power switch 170 may be a single switch for all powered system components, such as pumps 102, 130, 156; valves 150, 154, 152, 158; UV light source 22; and system interface 168 itself. Power switch 170 may also include a switch for each such component or sets of such components. System interface 168 includes at least one monitor 172 that displays a patient condition, such as the patient's venous pressure, arterial pressure, volume of blood drawn, blood temperature, etc. System interface 168 includes at least one alarm 174 that indicates when a patient condition is outside of a preferred range. A single alarm 174 may function to indicate several patient conditions or a separate alarm 174 may be included for more than one patient condition. System interface 168 may also include at least one user setting 176. User settings 176 allow the user to adjust or set parameters that affect the operation of system 100. User settings 176 may include presets. It is understood that the system interface 168 depicted in FIG. 4 is merely exemplary and that the system interface 168 may be arranged in many different configurations and its components, such as power switch 170, monitors 172, alarms 174, and user settings 176, may vary widely in their display.

Figure 5A:
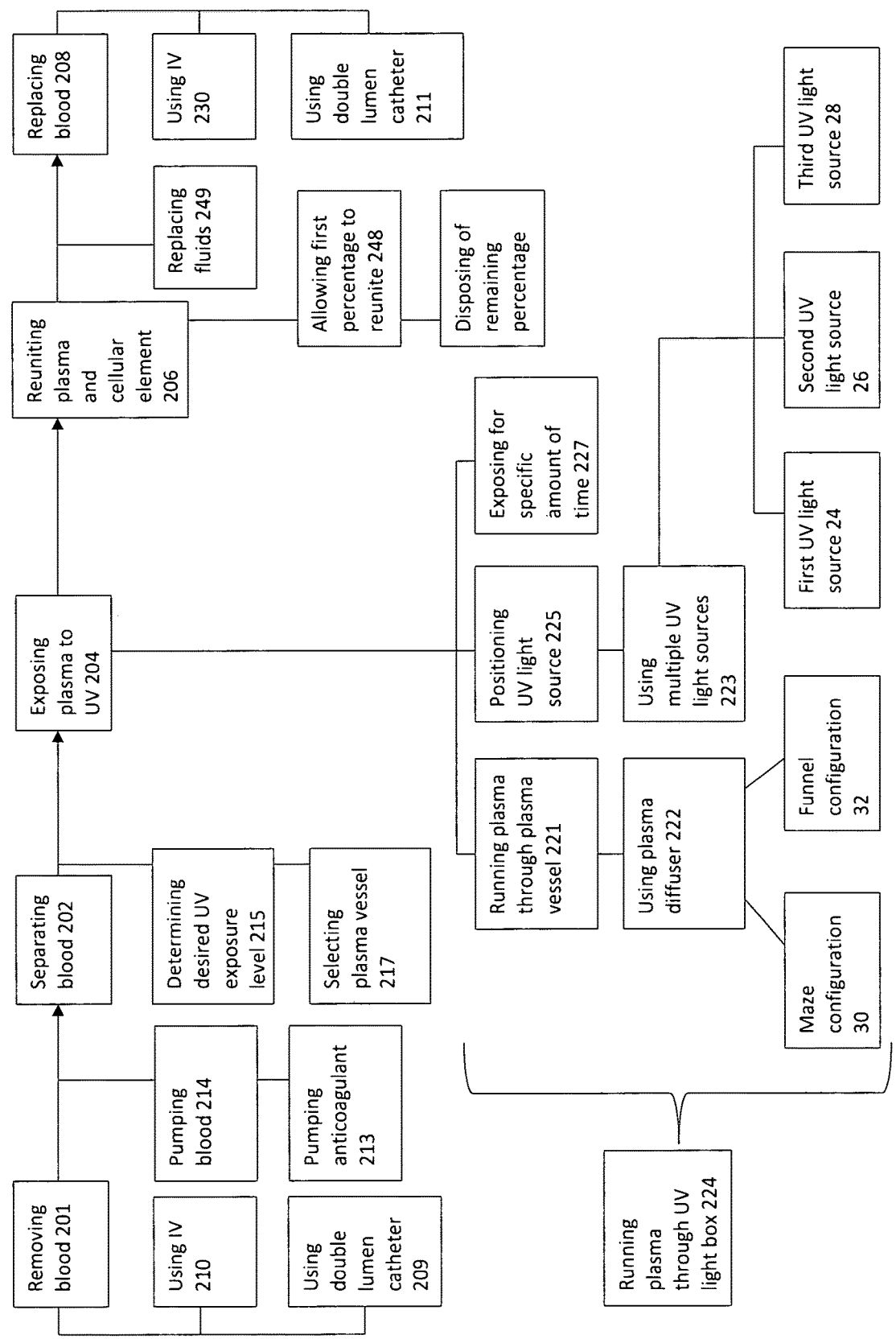
FIG. 5a is a flow chart indicating the steps of the method of the present invention when performed with the first configuration of the system of the present invention.

Now referring to FIG. 5a, a flow chart indicating the steps of method 200 of the present invention performed with the first configuration of the system of the present invention (as shown in FIG. 3a) is provided. The basic method 200 includes the steps indicated along the top of FIG. 5a: removing blood from a patient 201; separating the blood into plasma and a cellular element with a plasma separator 202; exposing the plasma to UV radiation 204; reuniting the irradiated plasma with the cellular element 206; and replacing the treated blood into the patient 208.

The step of removing the blood from the first patient 201 is performed by using intravenous (IV) venipuncture to remove blood from the patient 210 or using a double lumen catheter to remove blood from the patient 209. It is preferred that between the step of removing blood 201 and separating blood 202, method 200 also include the steps of pumping the blood into the plasma separator 214 and pumping anticoagulant into the blood 213. The step of replacing the treated blood into the second patient 208 is performed by IV venipuncture 230 or double lumen catheter 211. Method 200 preferably includes the steps of determining a desired level of UV exposure 215 and selecting a plasma vessel with a size and configuration that will effect the desired UV exposure level 217.

The step of exposing the plasma to UV radiation 204 includes the steps of running the plasma through a plasma vessel 221 and positioning at least one UV light source such that the at least one UV light source emits UV radiation onto the plasma vessel 225. The step of running the plasma through a plasma vessel 221 comprises the step of running the plasma through a plasma diffuser 222, in either a maze configuration 30 or a funnel configuration 32, as discussed with reference to FIGS. 2a and 2b, for examples. The step of positioning at least one UV light source 225 includes the step of using multiple UV light sources 223, such as first, second, and third UV light sources 24, 26, 28, each of which may emit different wavelengths of UV radiation, as discussed with reference to FIG. 1. The step of exposing the plasma to UV radiation 204 preferably comprises running the plasma through a UV light box 224 of the present invention, as detailed in FIG. 5c. The step of exposing the plasma to UV radiation 204 may include the step of exposing the plasma to UV radiation for a specific amount of time 227, as may be determined by factors such as pathogen load, targeted pathogen, and whether the aim is inactivation of death of the pathogen. The step of reuniting the plasma with the cellular element 206 may include the steps of allowing only a first percentage of the irradiated plasma to reunite with the cellular element 248; and disposing of the remaining percentage of the irradiated plasma 250. Method 200 preferably includes the step of replacing fluids 249 between the reuniting step 206 and the replacing step 208.

Figure 5B:
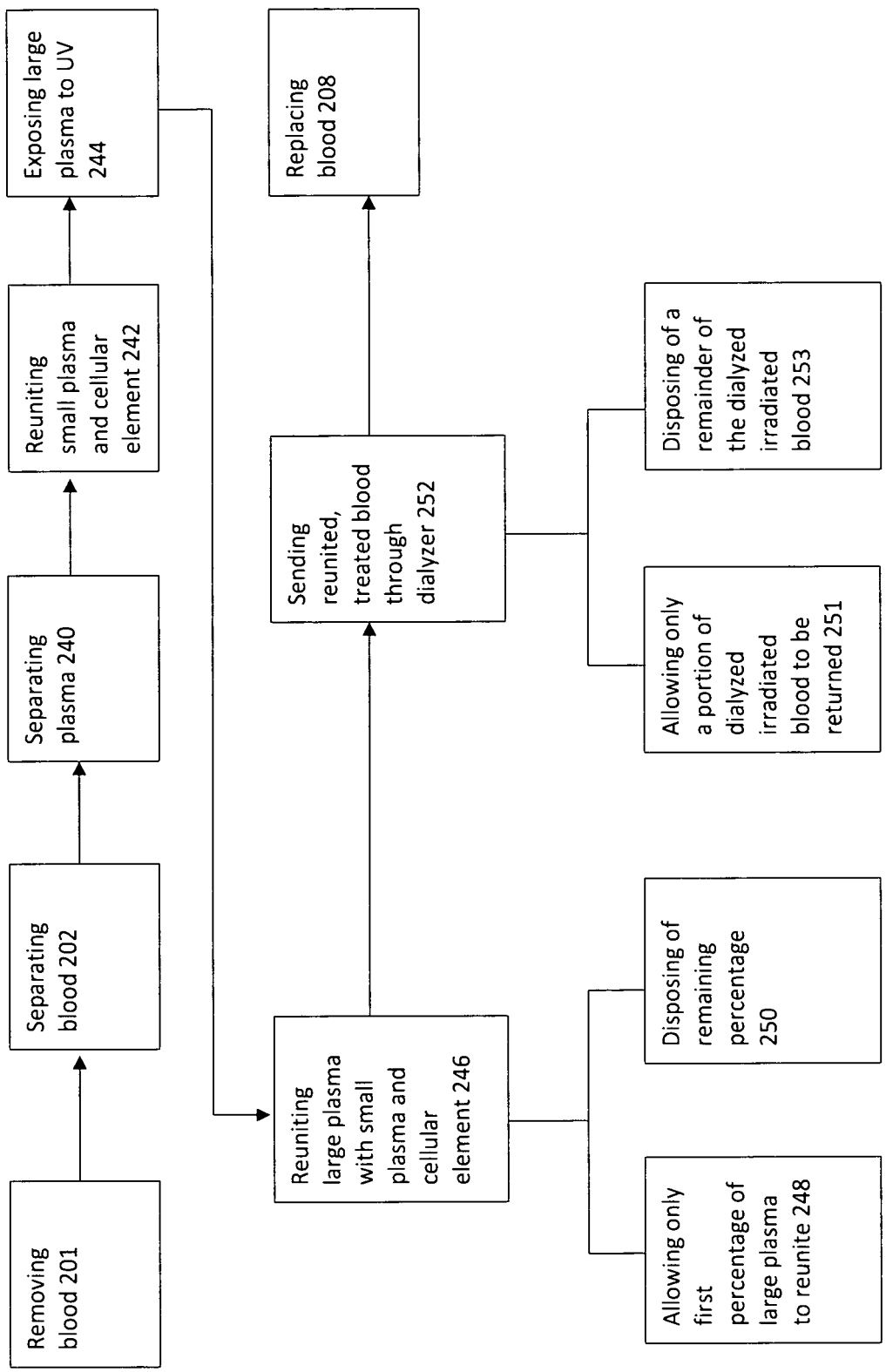
FIG. 5b is a flow chart indicating the steps of the method of the present invention when performed with the second and third configurations of the system of the present invention.

Now referring to FIG. 5b, a flow chart indicating the steps of method 200 of the present invention performed with the second and third embodiments of the system of the present invention (as shown in FIGS. 3b and 3c) is provided. The basic steps of method 200 and variations thereof, as described with respect to FIG. 5a above, remain the same. With the second and third embodiments of the system of the present invention, however, after the step of separating the blood 202, method 200 also includes the steps of separating the plasma into small plasma and large plasma with a plasma component separator 240; reuniting the small plasma with the cellular element 242; sending only the large plasma on to the step of exposing the plasma to UV radiation 244; and reuniting the large plasma with the small plasma and the cellular element 246.

When method 200 is performed using the third configuration of system 100, method 100 may include the step of sending the reunited, treated blood through a dialyzer 252; allowing only a portion of the dialyzed irradiated blood to be returned to the patient 251; and disposing of a remainder of the dialyzed irradiated blood 253.

Figure 5C:
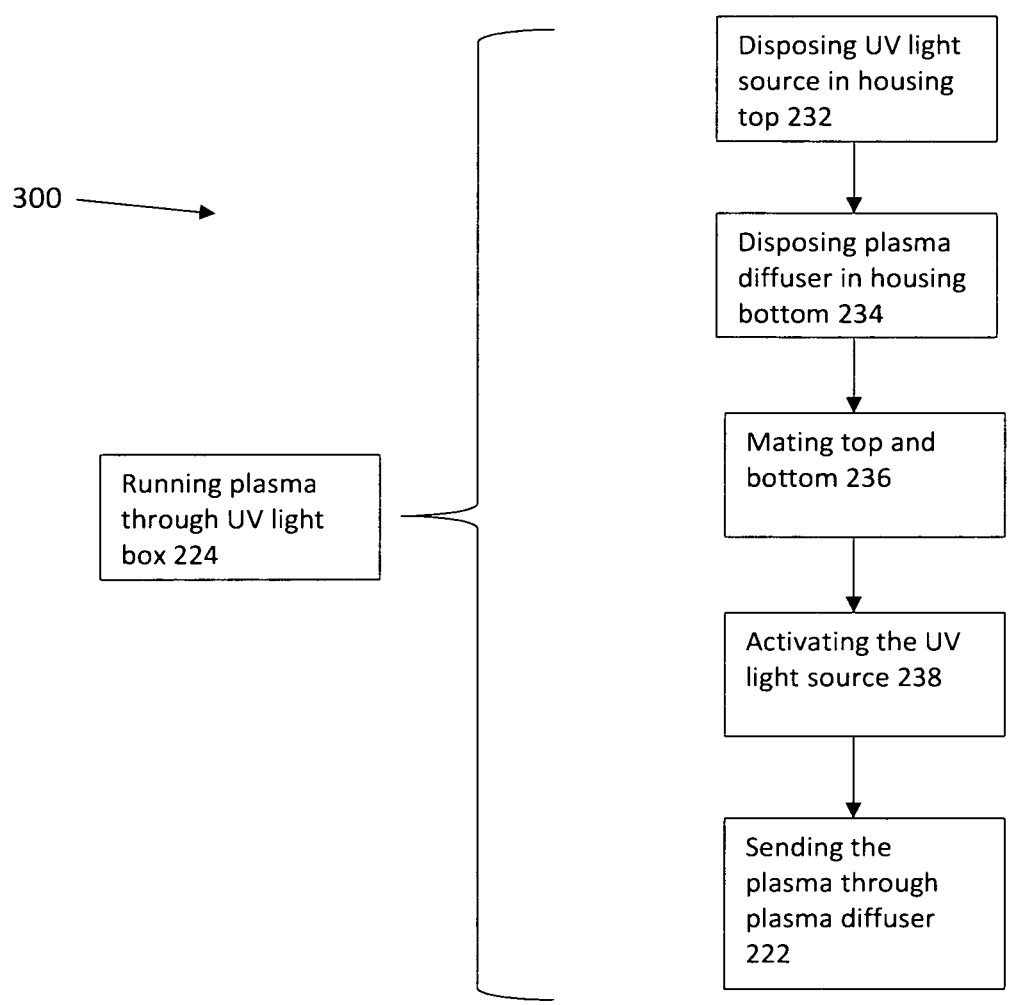
FIG. 5c is a flow chart indicating the steps of the UV box method of the present invention.

Now referring to FIG. 5c, the steps of method 300 for irradiating plasma using a UV box are provided. These steps detail step 224, shown in FIG. 5a, but are also independent method 300. The steps of method 300 include disposing at least one UV light source in the top of a housing 232; disposing a plasma diffuser in the bottom of the housing 234; mating the top and bottom of the housing so that the UV light source and the plasma diffuser face one another 236; activating the UV light source 238; and sending the plasma through the plasma diffuser 222. Options regarding the plasma diffuser 16 and UV light source 22 are as described with respect to FIGS. 1 and 5c.

Although the present invention has been described in considerable detail with reference to certain preferred versions thereof, other versions would be readily apparent to those of ordinary skill in the art. Therefore, the spirit and scope of the description should not be limited to the description of the preferred versions contained herein.

I claim:

1. A method for irradiating blood, comprising the steps of:
   removing blood from a patient;
   separating the blood into plasma and a cellular element with a plasma separator;
   separating the plasma into small plasma and large plasma with a plasma component separator;
   reuniting the small plasma with the cellular element;
   positioning at least one ultraviolet (UV) light source such that the at least one UV light source emits, and exposes the large plasma to, UV radiation;
   reuniting at least a portion of the irradiated large plasma with the cellular element and small plasma; and
   replacing the treated blood into the patient.

2. The method as claimed in claim 1, wherein said step of removing blood from a first patient comprises using a central line double lumen catheter to remove blood from the patient.

3. The method as claimed in claim 1, wherein said step of exposing the large plasma to at least one UV light source comprises the steps of:
   sending at least a portion of the large plasma through a plasma vessel; and
   positioning the at least one UV light source such that the at least one UV light source emits UV radiation on the plasma vessel.

4. The method as claimed in claim 3, further comprising the steps of before said step of exposing the large plasma to at least one UV light source:
   determining a desired UV exposure level; and
   selecting a plasma vessel with a size and configuration that will effect the desired UV exposure level;
   wherein, said step of sending at least a portion of the large plasma through a plasma vessel comprises sending at least a portion of the large plasma through the plasma vessel selected in said step of selecting a plasma vessel with a size and configuration that will effect the desired UV exposure level.

5. The method as claimed in claim 3, wherein said step of sending at least a portion of the large plasma through a plasma vessel comprises sending at least a portion of the large plasma through a plasma diffuser.

6. The method as claimed in claim 5, wherein said step of sending at least a portion of the large plasma through the plasma diffuser comprises sending at least a portion of the large plasma through a maze configuration plasma diffuser.

7. The method as claimed in claim 5, wherein said step of sending at least a portion of the large plasma through the plasma diffuser comprises sending at least a portion of the large plasma through a funnel configuration plasma diffuser.

8. The method as claimed in claim 1, wherein said step of exposing the large plasma to at least one UV light source comprises the step of exposing the large plasma to at least a first UV light source and a second UV light source, wherein:
   the first UV light source emits a first wavelength;
   the second UV light source emits a second wavelength; and
   the first and second wavelengths are not equal.

9. The method as claimed in claim 8, wherein said step of exposing the large plasma to at least a first UV light source and a second UV light source comprises the step of exposing the large plasma to at least a first UV light source, a second UV light source, and a third UV light source, wherein:
   the third UV light source emits a third wavelength; and
   the third wavelength is not equal to at least one of the first and second wavelengths.

10. The method as claimed in claim 3, wherein said step of sending at least a portion of the large plasma through the plasma diffuser such that the at least one UV light source emits UV radiation on the plasma diffuser comprises the steps of:
    disposing the at least one UV light source in a top of a housing;
    disposing the plasma diffuser in a bottom of the housing, wherein the top and the bottom of the housing are sized and configured to mate;
    mating the top and bottom of the housing such that the at least one UV light source and the plasma diffuser face one another;
    activating the at least one UV light source; and
    sending at least a portion of the large plasma through the plasma diffuser.

11. The method as claimed in claim 1, wherein said step of replacing the treated blood into the patient comprises using a central line double lumen catheter to replace blood into the patient.

12. The method as claimed in claim 1, further comprising the step of after said step of removing blood from a patient and before said step of separating the blood into plasma and a cellular element with a plasma separator, pumping the blood into the plasma separator.

13. The method as claimed in claim 1, wherein said step of reuniting at least a portion of the irradiated large plasma with the cellular element and the small plasma comprises the steps of:
    allowing only a first percentage of the irradiated large plasma to reunite with the cellular element and the small plasma; and
    disposing of a remaining percentage of the irradiated large plasma.

14. The method as claimed in claim 1, further comprising the step of sending the treated blood through a dialyzer.

15. The method as claimed in claim 14, further comprising the steps of:

allowing only a second portion of the dialyzed blood to said step of replacing the treated blood into the patient; and disposing of a second remainder of the dialyzed first portion of the irradiated large plasma.

16. The method as claimed in claim 1 further comprising the step of replacing fluid into the treated blood.

17. The method as claimed in claim 1, further comprising the step of after said step of removing blood from a patient and before said step of separating the blood into plasma and a cellular element with a plasma separator, pumping anticoagulant into the blood.

\* \* \* \* \*